(12) United States Patent
Pirovano et al.

(10) Patent No.: US 7,744,566 B2
(45) Date of Patent: Jun. 29, 2010

(54) SYSTEM OF INFUSION OF PHARMACOLOGICAL SOLUTIONS

(75) Inventors: Marco Pirovano, Milan (IT); Stefania Improta, Rome (IT)

(73) Assignee: H.S. Hospital Services S.p.A., Aprilia (LT) (IT)

( * ) Notice: Subject to any disclaimer, the term of this patent is extended or adjusted under 35 U.S.C. 154(b) by 0 days.

(21) Appl. No.: 10/563,909

(22) PCT Filed: Jul. 9, 2004

(86) PCT No.: PCT/IB2004/002245

§ 371 (c)(1),
(2), (4) Date: Jan. 10, 2006

(87) PCT Pub. No.: WO2005/004953

PCT Pub. Date: Jan. 20, 2005

(65) Prior Publication Data

US 2006/0167404 A1    Jul. 27, 2006

(30) Foreign Application Priority Data

Jul. 11, 2003   (IT) .................... MO2003A0201

(51) Int. Cl.
*A61M 37/00*   (2006.01)
(52) U.S. Cl. .................. 604/131; 604/151; 604/246
(58) Field of Classification Search .............. 604/500, 604/503, 506, 65, 66, 67, 131, 133, 151, 604/246, 247
See application file for complete search history.

(56) References Cited

U.S. PATENT DOCUMENTS

| | | | |
|---|---|---|---|
| 2,979,055 A | | 4/1961 | De Beer et al. |
| 3,252,623 A | * | 5/1966 | Corbin et. al. .............. 222/59 |
| 4,270,532 A | * | 6/1981 | Franetzki et al. ............ 604/151 |
| 4,386,929 A | | 6/1983 | Peery et al. |
| 4,559,036 A | * | 12/1985 | Wunsch ....................... 604/81 |
| 4,673,389 A | | 6/1987 | Archibald et al. |
| 4,741,732 A | * | 5/1988 | Crankshaw et al. ......... 604/503 |
| 4,976,687 A | | 12/1990 | Martin |

(Continued)

FOREIGN PATENT DOCUMENTS

EP    0 885 620    12/1998

(Continued)

OTHER PUBLICATIONS

International Search Report for PCT/IB2004/002245 dated Jan. 10, 2005.

*Primary Examiner*—Kevin C Sirmons
*Assistant Examiner*—Bhisma Mehta
(74) *Attorney, Agent, or Firm*—Nixon & Vanderhye P.C.

(57) ABSTRACT

A system for the infusion of pharmacological solutions includes a container to contain a pharmacological solution, a pumping device for generating a flow of pharmacological solution from the container, an adjusting device to vary the flow and a command and control device operationally associated with the adjusting device. A method for the infusion of a pharmacological solution in a patient includes generating a flow of pharmacological solution from a container containing the pharmacological solution, sending the flow to a catheter insertable in the patient, adjusting the flow by an adjusting device actuated by a command and control device, and programming the flow and infusion times using a programming device operationally connected to the command and control device.

18 Claims, 5 Drawing Sheets

U.S. PATENT DOCUMENTS

| | | | |
|---|---|---|---|
| 6,367,502 B1 * | 4/2002 | Kanai et al. ................. | 137/556 |
| 2002/0045856 A1 | 4/2002 | Jaafar et al. | |
| 2003/0018304 A1 | 1/2003 | Sage | |

FOREIGN PATENT DOCUMENTS

| | | |
|---|---|---|
| EP | 0 947 208 | 10/1999 |
| GB | 2 309 801 | 8/1997 |
| WO | 88/00841 | 2/1988 |

\* cited by examiner

SYSTEM OF INFUSION OF PHARMACOLOGICAL SOLUTIONS

This application is the U.S. national phase of international application PCT/IB2004/002245 filed 9 Jul. 2004, which designated the U.S. and claims priority to IT MO2003A000201 filed 11 Jul. 2003, the entire contents of each of which are hereby incorporated by reference.

The present invention relates to a system for the infusion of pharmacological solutions, i.e. a system for performing continuous or intermittent subcutaneous, endovenous, intraarterial or epidural infusions of pharmacological solutions, with a variable and programmed preset flow, for example on the basis of the patient's circadian rhythms, or something else, or constant-flow infusions.

It is known that the human organism transforms, uses and eliminates drugs according to the levels of activity of the enzymatic and excretory apparatuses. The level of activity of these apparatuses oscillates at a constant rhythm over 24 hours (circadian rhythm). It is thus possible to determine the optimum infusion profiles according to the circadian rhythm of the patient to obtain greater efficacy from the same treatment with as little toxicity as possible. Currently, the infusion of pharmacological solutions is achieved through widespread use of pumps, in particular mechanical pumps such as elastomeric and spring pumps for constant-flow infusions, and electromechanical pumps such as peristaltic or impeller pumps for variable-flow infusions.

The use of electromechanical pumps for variable-flow infusions has numerous drawbacks. Firstly, the relevant dimensions and the considerable weight make these pumps very inconvenient to carry, with consequently significant problems of walking for the patient. These pumps furthermore have a high cost and require maintenance that is also costly, which significantly limits their use both in hospital facilities and for treatment at home.

The object of the present invention is to provide a system of infusion of pharmacological solutions that has a simple and reliable concept, is of moderate cost and can easily be carried by the patient.

A further object of the present invention is to provide a method for programming said system for the purpose of automatically performing one or more infusion protocols.

According to a first aspect of the present invention a system is provided for the infusion of pharmacological solutions comprising a containing arrangement suitable for containing a pharmacological solution, a pumping device for generating a flow of said pharmacological solution from said containing arrangement, wherein it furthermore comprises an adjusting device, to vary said flow and a command and control device operationally associated with said adjusting device.

Owing to the command and control device associated with the adjusting device it is possible to programme the trend over time of the flow of pharmacological solution according to preset curves, obtained for example on the basis of the patient's circadian rhythms.

In an advantageous embodiment of the present invention said adjusting device comprises at least one solenoid valve.

The use of solenoid valve makes adjustment of the flow of the pharmacological solution extremely simple.

In a further advantageous embodiment of the present invention said solenoid valve is of the normally closed type.

The use of a valve of the normally closed type has the advantage of immediately interrupting the delivery of the pharmacological solution if a fault occurs in the command and control device, for example an interruption to the electricity supply.

According to a further advantageous embodiment of the present invention, said command and control device commands a pulsed actuation of said solenoid valve, said flow being determined by the number of actuations of the solenoid valve in the time unit.

This feature enables very precise and safe adjustment of the flow of pharmacological solution, with negligible variations from the theoretical curve of desired flow.

According to another advantageous embodiment of the present invention, said solenoid valve comprises a solenoid arranged outside the valve part wherein the flow of pharmacological solution transits.

This enables the pharmacological solution not to be crossed by the electromagnetic field of the solenoid of the valve, which prevents ionization of the substances contained in the pharmacological solution, which may be harmful for the patient.

According to a further advantageous embodiment of the present invention, said pumping device comprises an elastomeric container wherein said pharmacological solution is inserted.

The elastomeric container, when it has been filled with the pharmacological solution, exerts a pressure on the solution that has a substantially constant value that pushes the solution into the infusion circuit and through the solenoid valve. The elastomeric container is chosen in such a way that the pressure that it exerts on the pharmacological solution is of a value such as to overcome the load losses present in the infusion circuit and in the solenoid valve.

In a further advantageous embodiment of the present invention, said command and control device is operationally associated with a plurality of solenoid valves, each one of which is associated with a different infusion circuit.

This enables the infusion of a plurality of pharmacological solutions to be piloted at preset times and with preset methods for each single solution, making extremely simple the implementation of treatments in which, over a given interval of time, a plurality of drugs has to be administered to the patient according to methods and times that vary for each single drug.

In a further advantageous embodiment of the present invention, said command and control device comprises an interface element for connecting the command and control device with a data processing system.

Through this feature, the system according to the invention can be used for a plurality of successive infusions, with different drugs and methods of administration that differ each time.

Furthermore, it is possible to monitor the administration of the pharmacological solution by means of the data-processing system and test the desired administration curve of the pharmacological solution.

According to a further aspect of the present invention a method is provided for the infusion of a pharmacological solution in a patient comprising generating a flow of said pharmacological solution from a container containing said pharmacological solution, sending said flow to a catheter inserted in the body of said patient, adjusting said flow by an adjusting device, wherein it furthermore comprises programming said flow and infusion times by means of a programming device acting on said adjusting device.

The invention will now be described below solely by way of non-limiting example, with reference to the table of enclosed drawings, in which:

FIG. 2 is a flow diagram that illustrates in general programming of the system according to the invention;

FIG. 3 is a flow diagram that illustrates the so-called "self-learning" procedure quoted in the diagram in FIG. 2;

FIG. 4 illustrates the setting procedure for the dosage curves provided for by the infusion protocol and FIG. 5 illustrates the setting procedure for infusion cycles provided for by the infusion protocol.

Figure 1:
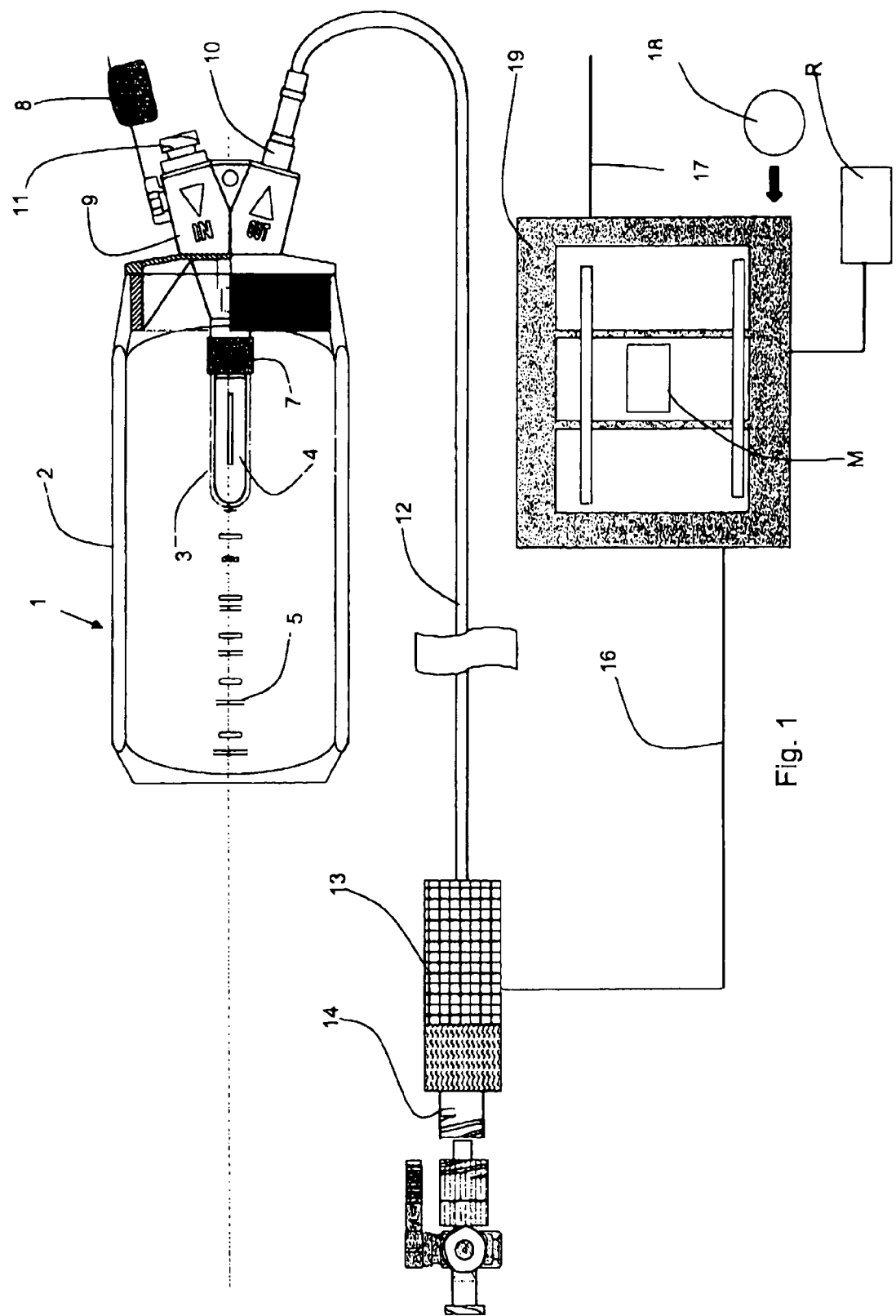
FIG. 1 is a schematic view of the system according to the invention.
Figure 2:
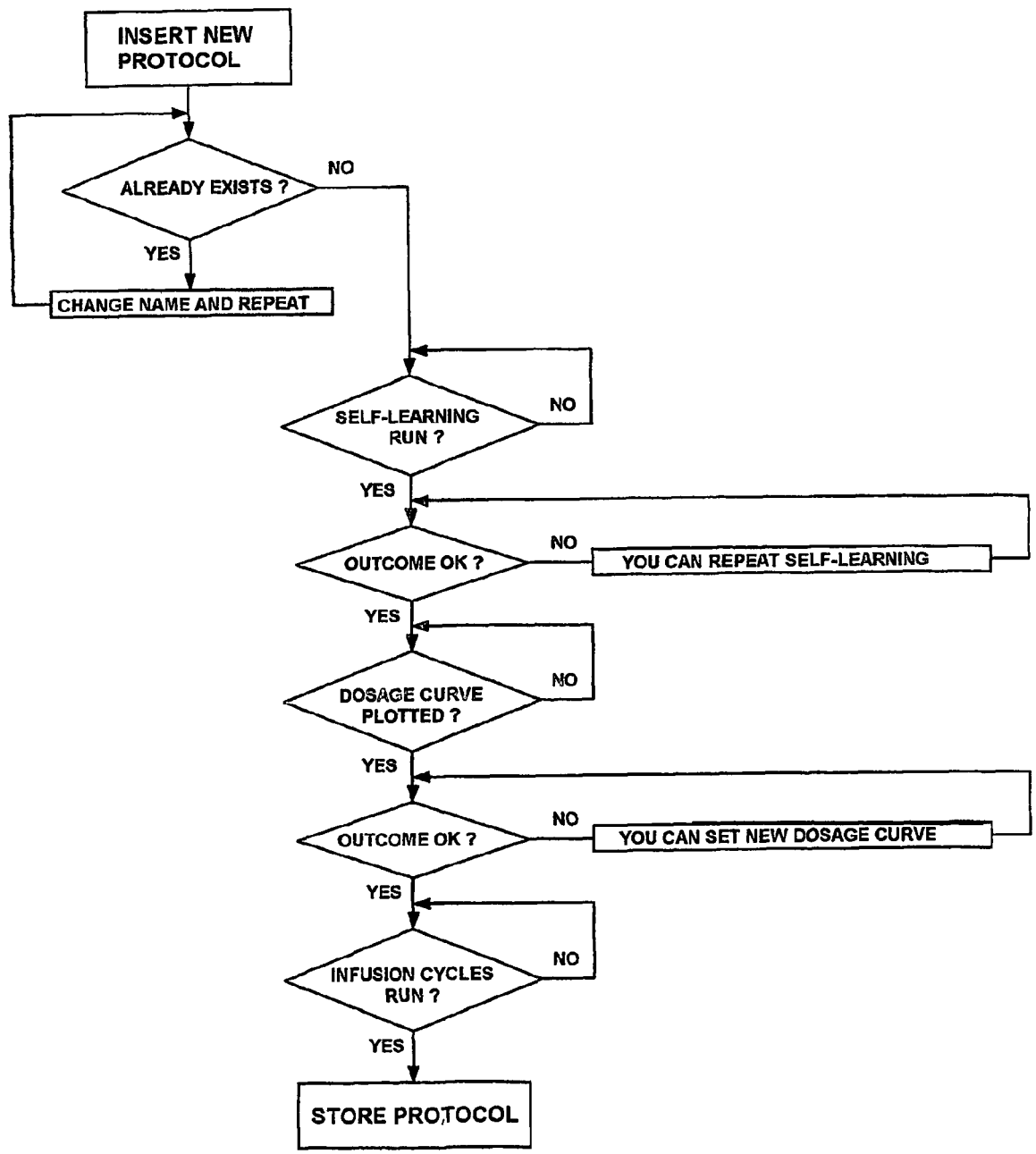
FIGS. 2, 3, 4 and 5 are flow diagrams that illustrate the programming of the system according to the invention; in particular
Figure 3:
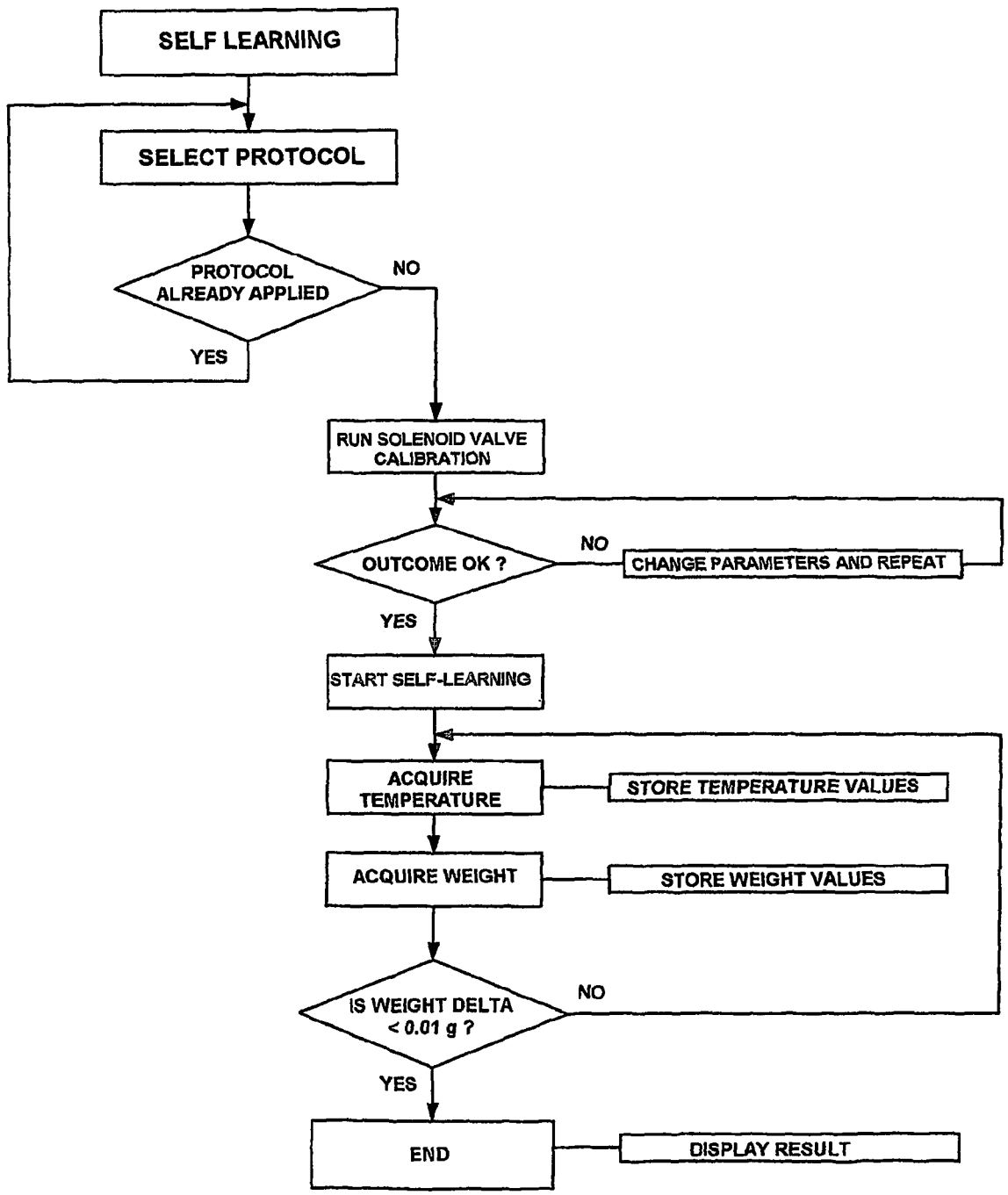
Figure 4:
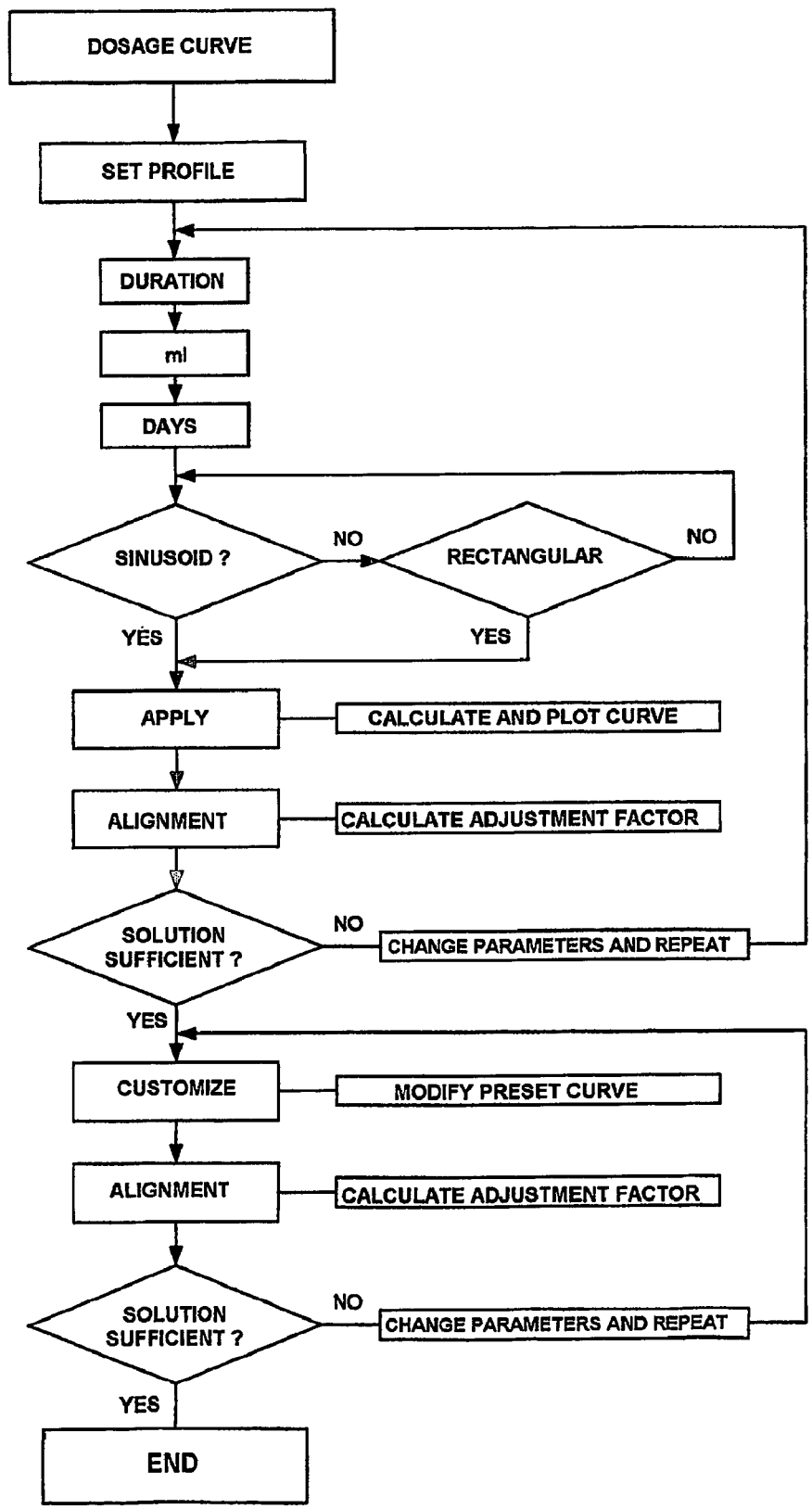
Figure 5:
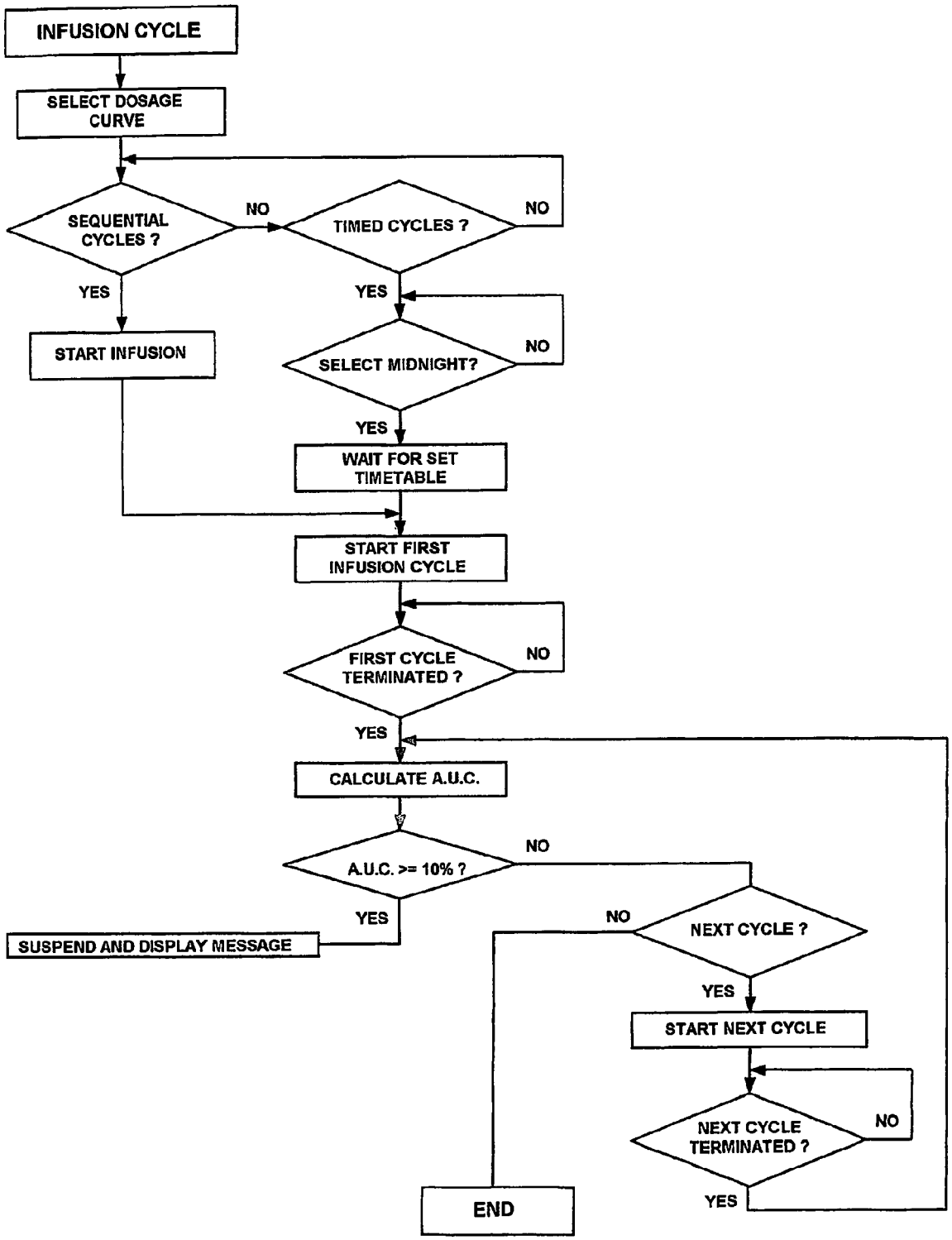

With reference to FIG. 1, the system according to the invention comprises a pumping device 1, comprising an elastomeric container 3, fixed to a support 4 provided with fixing and closing elements 7, and inserted into a containing and protection element 2 suitable for housing the elastomeric container 3 when the latter dilates through the effect of the introduction of the pharmacological solution and for protecting it from accidental damage.

The containing and protection element 2 is preferably made of transparent material and is provided on its external surface with a graduated scale 5 that enables the monitoring of the quantity of pharmacological solution introduced into the elastomeric container 3 and of the quantity of solution used during the infusion.

The protecting element 2 comprises an inlet portion 9 for introducing a pharmacological solution into the elastomeric container 3. The inlet portion 9 is provided with a check valve (not shown) to prevent pharmacological solution introduced into the elastomeric container 3 possibly flowing back through the inlet portion 9 through the effect of the pressure exerted thereupon by the walls of the elastomeric container 3. The inlet portion 9 is furthermore provided with a connecting element 11, for example a connecting element of the "luer-lock" type, that can be coupled with a delivery device such as for example a syringe to introduce the pharmacological solution to the elastomeric container 3. The inlet portion 9 may be equipped with a closing element 8, for example a plug, that can be removed only when the pharmacological solution has to be introduced into the elastomeric container 3.

The protecting element 2 furthermore comprises an outlet portion 10 through which the pharmacological solution introduced into the elastomeric container 3 can flow out thereof through the effect of the pressure exerted thereupon by the walls of the container 3.

The outlet portion 10 can be connected to a first end of a fitting element 12, for example a joint pipe, a second end of which is connected to a valve arrangement 13, the function of which is to adjust the flow of pharmacological solution exiting the elastomeric container 3.

The valve arrangement 13 may comprise a solenoid valve of the normally closed type.

To prevent the components of the pharmacological solution from being ionized by the electromagnetic field of the solenoid, it is advantageous that the latter be positioned outside the portion of valve in which the pharmacological solution transits.

The valve 13 may be connected to a venous or arterial catheter to be inserted into a vein or into an artery of a patient, for administration of the pharmacological solution.

Between the valve 13 and the catheter a three-way tap 14 may be interposed to stop the flow of pharmacological solution, enable the transit of the pharmacological solution into the catheter, or deviate said flow elsewhere.

The valve 13 is piloted by a command and control device 19, also called piloting device, connected electrically, by means of an electrical connection 16 to the solenoid of the valve 13.

The piloting device 19 comprises a microprocessor M to pilot the valve 13, that sends sequences of pulses to the solenoid of the valve that cause corresponding opening and closing of the valve. The flow of pharmacological solution that passes through the valve 13 and is sent to the catheter inserted into the body of the patient is proportional to the number of openings and reclosings of the valve 13 in the time unit, i.e., to the number of pulses in the time unit that the piloting device 19 sends to the valve 13.

The piloting device 19 can be set for piloting a single valve 13, or a plurality of valves 13, if an infusion of a plurality of pharmacological solutions has to be given according to preset times and methods.

As, in general, said solutions have to be infused at different times and with different methods, the piloting device 19 will be programmed to actuate the respective valves 13 according to the times and methods required for the infusion cycle that is to be run.

The system according to the invention may be of the disposable type, i.e. be usable for a sole infusion cycle, with one or more pharmacological solutions. In this case the piloting device 19 is preferably supplied by an electric supply apparatus comprising a battery 18, inserted into the piloting device 19. The duration of the battery 18 will preferably be chosen according to the duration of the infusion cycle to be run.

Alternatively, the system according to the invention may be of the multiple use type, i.e. usable for several infusion cycles for the same patient or for several patients. In this case, the piloting device 19 may be supplied by a rechargeable or replaceable source of supply and may also be connected by means of a suitable connecting element 17 to a data processing apparatus, by means of which it is possible to modify programming of the microprocessor, to run different infusion cycles for the same patient of for different patients, monitoring the trend of the infusion cycles, testing new infusion cycles for the purpose of adapting them to the specific physiology of the patient for whom they are intended, etc.

The piloting device 19 can be associated with a reading device R suitable for receiving a data recording support, for example a smart-card, on which data are stored for programming the microprocessor. In this way programming of the microprocessor may occur both from a remote station and by means of said data recording support.

In the case of a multiple use system it is furthermore advantageous to provide a washing arrangement to eliminate from the fitting element 12 and from the valve 13 residue of pharmacological solution, before using the system for the infusion of a new pharmacological solution.

The flow diagrams of FIGS. 2 to 5 illustrate the manner in which the system according to the invention is programmed to run one or more infusion cycles of a pharmacological solution.

Programming can be fixed, for the disposable systems, i.e. intended to run a single cycle or group of infusion cycles on a single patient. Alternatively, programming may be modifiable, if the piloting device of the system according to the invention is associated with a reading device for a data-storage support or is connectable to a personal computer.

To program the system according to the invention for an infusion protocol, proceed as follows.

A container 3 containing a preset quantity of pharmacological solution is inserted into the support 4 by connecting the container 3 to the inlet of the valve 13 by means of the fitting element 12 and the outlet of the valve 13 to a conduit that emerges in a container placed on an electronic balance.

At this point one proceeds to set and test a new infusion protocol.

Above all, the system according to the invention checks that the new protocol to be stored has not already been stored in the microprocessor of the piloting device 19, and if it has not an identifier is stored in the microprocessor such as a name of the new infusion protocol, an identifier of the type of pharmacological solution to be used and the maximum quantity in volume of pharmacological solution to be delivered on the basis of the new infusion protocol.

After carrying out the storage of the aforementioned data concerning the new infusion protocol, the solenoid valve is calibrated by conducting a series of openings and reclosings of the valve 13 with preset duration and at preset intervals of time, then comparing the quantity of solution delivered by the valve 13 with a theoretical preset value. If the quantity of solution delivered by the valve 13 differs from the theoretical preset value by a quantity greater than a preset quantity the aforementioned durations and intervals are varied until the quantity of delivered solution is not different from the theoretical amount by a quantity less than said preset quantity. If, however, it is not possible to reach this result within a preset time, an error signal is activated that indicates a solenoid valve fault.

After successful calibration of the solenoid valve, the so-called self-learning procedure is run, over the course of which it is checked that at each opening of the solenoid valve 13 a preset quantity in weight of pharmacological solution is delivered, storing for each of said openings also the temperature of the solution. This procedure is used to ascertain that there are no irregularities in the delivery of the pharmacological solution that are not detectable in the calibrating procedure.

At each opening of the solenoid valve 13, the weight of delivered solution is compared with a reference value, from which it must not deviate by a quantity greater than a set quantity. If the deviation is greater than said preset quantity for a preset number of opening cycles of the valve 13, the self-learning procedure is stopped by a solenoid valve fault message.

Otherwise, the procedure is continued until the complete emptying of the container 3, then ascertaining that the system is able to correctly deliver the maximum quantity of pharmacological solution provided for by the infusion protocol.

At the end of the self-learning procedure, the dosage curve of the pharmacological solution provided for by the infusion cycle and the parameters of the infusion cycle are set.

Above all, the profile of the curve is set by fixing the duration of the infusion curve, the volume of pharmacological solution that has to be injected on the basis of the infusion curve and the number of days, i.e. the number of repetitions at daily intervals of the infusion curve, provided for by the infusion protocol. The type of infusion curve to be plotted for example sinusoid or square wave, or other, is then selected from a preset group of curve types. The system then calculates the theoretical number, duration and distribution of the opening cycles of the solenoid valve 13 required to plot the infusion curve of which the profile has been set. Subsequently, the quantity of pharmacological solution is calculated that is delivered by the dosage curve and it is ascertained that this quantity is not greater than what is available in the container 3. In the latter case, the curve parameters are modified to determine an adjustment factor of the curve in such a way as to make the quantity delivered fall within the quantity available in the container.

Lastly, the dosage curve may be customized on the basis of the particular requirements of the patient. The last procedure to be conducted concerns the setting of the parameters of the infusion cycle that has to be run on the basis of the chosen protocol.

Above all, the type of dosage curve for the selected infusion cycle is selected, then one selects whether the infusion cycle should start as soon as the startup of the system or at a preset time, indicating in the latter case whether the infusion cycle has to start on the day on which the system is started up or the day after.

Before storing the parameters of the infusion cycle the actual quantity of pharmacological solution delivered by the system may be checked by comparing it with the theoretical quantity that should have been delivered according to the infusion cycle. To that end, the infusion cycle is started and one checks at preset time intervals whether or not the cycle has terminated. At the end of the cycle the system ascertains whether the quantity of pharmacological solution provided for by the protocol has been delivered. If the quantity of pharmacological solution (A.U.C) delivered differs from the theoretical quantity to be delivered by a quantity that is greater than a preset value, for example by more than 10%, an error signal is activated, otherwise the next infusion cycle is started up, if provided for by the protocol. After all the infusion cycles provided for by the protocol have terminated and the quantity of pharmacological solution actually delivered has been ascertained for each cycle, the infusion protocol is stored.

The stored protocol is not modifiable; if modifications have to be made, a new protocol containing the aforementioned modifications must be stored.

The protocol can be stored on a personal computer connectable to the system according to the invention, or, if the system according to the invention is provided with a reading device of a data-storage support, the protocol can be stored on said data-storage support. If the infusion protocol is stored on a personal computer, the latter will transmit to the microprocessor of the command and control device the data on the infusion cycle, when the system has to run the aforementioned cycle. If, on the other hand, the protocol has been stored on a data-storage support, the transmission to said microprocessor of the data on said protocol is achieved by inserting the data-storage support into the aforementioned reading device, in such a way that the data can be read by the microprocessor.

Lastly, if the system is of the disposable type, the protocol is stored directly in the microprocessor of the piloting device.

In the practical embodiment, the materials, dimensions and constructional details may be different from those shown but be technically equivalent, without thereby departing from the legal scope of the present invention.

The invention claimed is:

1. A system for the infusion of a pharmacological solution in a patient, comprising:
    an elastomeric container for containing a pharmacological solution and for generating a flow of the pharmacological solution from said container to a catheter insertable in the body of the patient, said elastomeric container, in use, exerting a pressure on the pharmacological solution that generates the flow;
    a valve arrangement to vary the flow;
    a command and control device operationally connected to said valve arrangement to command a pulsed actuation of said valve arrangement, the flow being determined by the number of actuations of said valve arrangement per unit time;
    an infusion protocol according to which the pulsed actuation is made, said infusion protocol being stored on a data-processing system or on a data-storage support, said stored infusion protocol being not modifiable; and said stored infusion protocol including at least an infusion curve, said infusion curve being defined by definition parameters comprising a duration of infusion, a volume of pharmacological solution to be infused, and a type of the infusion curve, wherein a number, a duration and a distribution of opening cycles of said valve arrangement are calculated to plot said infusion curve.

2. The system according to claim 1, wherein said valve arrangement comprises a valve of the normally closed type.

3. The system according to claim 1, wherein said valve arrangement comprises at least one solenoid valve.

4. The system according to claim 1, wherein said command and control device comprises a microprocessor operationally connected to said valve arrangement.

5. The system according to claim 1, wherein said elastomeric container is supported on a support element associated with a containing and protection element.

6. The system according to claim 5, wherein said containing and protection element is made of transparent material and is equipped on its outside surface with a graduated scale.

7. The system according to claim 5, wherein said containing and protection element comprises an inlet portion connected to said elastomeric container to introduce therein the pharmacological solution.

8. The system according to claim 7, wherein said inlet portion is associated with a connecting element suitable for enabling coupling of said inlet portion with an introducing device, to introduce the pharmacological solution into said inlet portion.

9. The system according to claim 7, wherein said containing and protection element furthermore comprises an outlet portion connected to said elastomeric container, through which the pharmacological solution introduced into the elastomeric container can flow out thereof.

10. The system according to claim 9, wherein said outlet portion is suitable for being connected to a first end of a fitting element, a second end of which is connected to said valve arrangement.

11. The system according claim 10, wherein said valve arrangement is associated with a further connecting element suitable for enabling coupling of said valve arrangement with a delivery device, for administration of the pharmacological solution.

12. The system according to claim 1, comprising an interface element for operationally connecting said command and control device with said data processing system.

13. The system according to claim 1, wherein said command and control device comprises a reading device suitable for receiving a data recording support and for reading data stored thereupon.

14. The system according to claim 13, wherein said data recording support is a data recording support of the smart-card type.

15. The system according to claim 1, comprising a battery to supply power to said command and control device.

16. The system according to claim 15, wherein said battery is of the rechargeable or replaceable type.

17. The system according to claim 1, wherein said command and control device comprises a microprocessor operationally connected to said valve arrangement, said infusion protocol being stored in said microprocessor.

18. The system according to claim 1, wherein the elastomeric container is structured or configured to exert a pressure on the pharmacological solution that has a substantially constant value.

* * * * *